United States Patent [19]

Camaggi et al.

[11] Patent Number: 4,628,101

[45] Date of Patent: Dec. 9, 1986

[54] COMPOUNDS HAVING A ANTIDOTE ACTIVITY FOR THE PROTECTION OF CULTIVATIONS OF AGRARIAN INTEREST FROM THE ACTION OF NONSELECTIVE HERBICIDES

[75] Inventors: Giovanni Camaggi, Lodi; Franco Gozzo, San Donato Milanese; Ernesto Signorini, Malnate; Ottorino Palla, Crema, all of Italy

[73] Assignee: Montedison S.p.A., Milan, Italy

[21] Appl. No.: 834,773

[22] Filed: Feb. 28, 1986

Related U.S. Application Data

[63] Continuation of Ser. No. 528,169, Aug. 31, 1983, abandoned.

[30] Foreign Application Priority Data

Sep. 1, 1982 [IT] Italy ............................ 23092 A/82
Jul. 12, 1983 [IT] Italy ............................ 22015 A/83

[51] Int. Cl.[4] .................. C07D 277/04; C07D 277/06

[52] U.S. Cl. .................................. 548/200; 548/201; 71/90

[58] Field of Search .................... 548/200, 201; 71/90

[56] References Cited

U.S. PATENT DOCUMENTS 4,137,066 1/1979 Gaughan .............................. 71/91
4,499,102 2/1985 Oya .................................. 514/365

*Primary Examiner*—Robert Gerstl

[57] ABSTRACT

Compounds having antidote activity and belonging to the class of the derivatives of 1,3-thiazolidine useful for protecting cultivations of agrarian interest from the toxic action of nonselective herbicides are herein described. The invention relates, also, to a method for protecting cultivations of agrarian interest from the toxic action of nonselective herbicides consisting in the use, as antidotes, of the above mentioned compounds and the compositions for agrarian use containing said compounds.

8 Claims, No Drawings

COMPOUNDS HAVING A ANTIDOTE ACTIVITY FOR THE PROTECTION OF CULTIVATIONS OF AGRARIAN INTEREST FROM THE ACTION OF NONSELECTIVE HERBICIDES

This is a continuation of application Ser. No. 528,169, filed Aug. 31, 1983, abandoned.

BACKGROUND OF THE INVENTION

The herbicides belonging to the class of chloracetanilides or of thiolcarbamates, are very useful compounds in the fight against plants infesting agarian cultivations.

Many of these herbicides exert, however, their toxic action also against certain useful cultivations such as for instance maize and sorghum and thus, not being selective, cannot be used for the weeding of said cultivations.

The availability of antidotes, that is, of compounds protecting the useful agrarian cultivations from the toxic action of said herbicides without at the same time reducing their herbicide action towards the infesting weeds, will allow the use of these herbicides also in the protection of those useful cultivations which otherwise would be damaged.

Among the main herbicides which prove phytotoxic for certain useful cultivations, there may be listed those belonging to the class of chloroacetanilides which comprises for instance: N-methoxymethyl-2,6-diethylchloroacetanilide (common name Alachlor), N-butoxymethyl-2,6-diethylchloroacetanilide (common name: "BUTACHLOR"), N-methoxyethyl-2-methyl-6-allylchloroacetanilide (reference item M8669) as well as the ones belonging to the class of the thiolcarbamates comprising, for example, N,N-diisopropyl-S-(2,3-dichloroallyl)-thiolcarbamate (common name: "DIALLATE"); N,N-diisopropyl-S-(2,3,3-trichloroallyl)-thiolcarbamate (common name "TRIALLATE"); N,N-diethyl-S-(4-chlorobenzyl)-thiolcarbamate (common name: "BENTHIOCARB"); N,N-dipropyl-S-ethyl-thiolcarbamate (common name: "EPTAM").

It is known that some compounds, belonging to different chemical classes, are capable of protecting useful cultivations from the toxic action exerted by herbicides. For instance, dichloroacetamides useful as antidotes have been described in U.S. Pat. No. 4,021,224 (Stauffer) or in U.S. Pat. No. 4,228,101 (Montedison S.p.A.); 2-chlorothiazoles disubstituted in position 4 and 5, useful as antidotes in the protection of sorghum cultivations, have been described in European Pat. No. 27,019 (Monsanto Co.).

THE PRESENT INVENTION

We have now found compounds, which form an object of this invention, having formula (I):

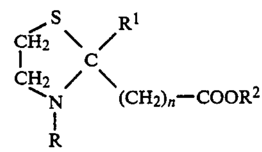

wherein:

R represents the group $$-\underset{\underset{O}{\|}}{C}-R^3$$

in which $R^3$ represents a $C_1$–$C_3$ haloalkyl containing from 1 to 3 halogen atoms or a phenyl group optionally substituted;

$R^1$ represents a hydrogen atom, a methyl or a phenyl;

$R^2$ represents a $C_1$–$C_8$ alkyl group, a $C_5$–$C_6$ cycloalkyl group, a cyclohexylmethyl group, a phenyl group optionally substituted, a benzyl group optionally substituted, an allyl or propargyl group;

n is zero or one; provided that when contemporaneously R is a haloacetyl group, $R^1$ is hydrogen and n is zero, $R^2$ be different from a $C_1$–$C_4$ alkyl.

The compounds excluded by the proviso have been described in our co-pending United States patent application No. 475,959, filed Mar. 16, 1983 and have antidote activity too.

The toxic action of nonselective herbicides belonging, for instance, to the class of the chloroacetanilides or of thiolcarbamates, towards useful cultivations, may be considerably reduced or even eliminated, without decreasing the herbicide activity against the infesting weeds, if a compound of formula I is used as an antidote.

Thus, a second object of the present invention consists in a method for reducing the damages on useful cultivations caused by nonselective herbicides belonging, for example, to the class of chloroacetanilides or of thiolcarbamates, a method which consists in treating the seeds, the plants or the soil where they grow with an effective amount of an antidote of formula I, either as such or in the form of suitable compositions.

Still another object of the present invention consists in a composition containing a compound of formula I, as an active ingredient, together with an inert carrier and optionally other additives, said composition being useful for the treatment of seeds of useful plants, of the plants themselves or of the soil where they grow.

A further object of the present invention consists in the seeds of useful plants treated with an effective amount of a compound of formula I.

The preparation of the compounds of formula I is conveniently carried out by reacting cysteamine (II) with an α- or β-keto-ester (III) and by subjecting to acylation with the suitable acyl-chloride the 1,3-thiazolidine derivative (IV) obtained by the first reaction:

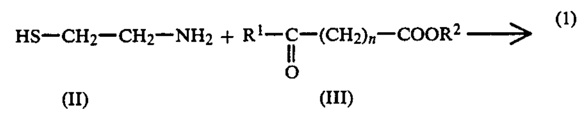

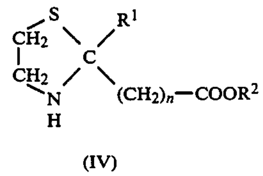

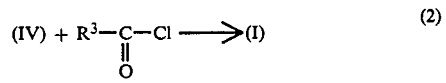

($R^1$, $R^2$, $R^3$ and n have the meanings reported for formula I).

Reaction 1 is carried out in a polar solvent, in the presence of a base and at a temperature comprised between room temperature and the boiling temperature of the reaction mixture.

Reaction 2 is a common acylation reaction carried out in an inert solvent and in the presence of a halogenhydric acid-accepting base.

The compounds of formula III are esters of known carboxylic acids such as formyl-acetic acid ($R^1$=H, n=1), acetacetic acid ($R^1$=H, n=1), benzoyl-acetic acid ($R^1$=phenyl, n=1), glycolic acid ($R^1$=H, n=0), pyruvic acid ($R^1$=$CH_3$, n=0), phenylglycolic acid ($R^1$=phenyl, n=0).

Some of the compounds of formula IV are known in the form of free acids or lower alkyl esters (see for example, E. Bieker et al., Chem Ber. 95, 1466 (1962) Chem. Abst.s 57. 7244i and R Tondeur et al., Bull. Soc. Chim. F. 2495 (1964) Chem. Abst.s. 62: 5264 b).

It is clear to a person skilled in the art how the preparation of the compounds of formula I may be carried out also by alternative procedures like, for example, by preparing the free acid and by the esterification of this latter with the selected alcohol, or by transesterification or still by inserting the order between cyclization and acylation (reactions 1 and 2 hereabove).

In this latter case the compound of formula III is made to react with an acylated cysteamine prepared by acylation of cysteamine after having preliminary protected the SH group.

Specific examples of compounds of formula I are the following:

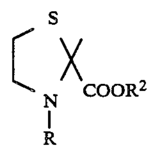

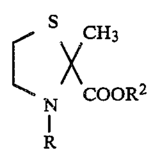

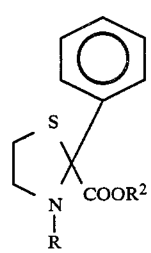

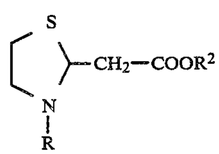

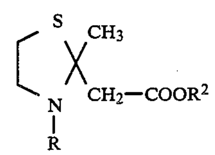

-continued

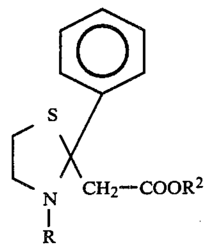

wherein R and $R^2$ have the meanings above reported for formula I and in particular R may be a dichloroacetyl group ($R^3$=$CHCl_2$) or a benzoyl group ($R^3$=phenyl) optionally substituted.

Among the optional substituents of the aromatic nucleus, (when $R^3$ is a phenyl optionally substituted and when $R^2$ is an optionally substituted phenyl or benzyl) there may be cited from one to three substituents selected from $C_1$–$C_4$ alkyl, $C_1$–$C_4$ alkoxy, nitro, trifluoromethyl and halogen, in particular chlorine and bromine.

As hereabove mentioned, the antidotes of formula I may be applied to the useful cultivations following different procedures.

For instance they may serve for a preventive treatment of the seeds so that the plant that develops will be protected from the toxic action of the non selective herbicides.

Alternatively, the compounds of formula I may be used for the treatment of the useful plant itself or of the soil where it grows.

In this case, the antidote may be applied alone or in combination with the nonselective herbicide, separately or in a single composition.

The different types of application require different conditions which reflect on the practical aspects of the treatment, such as for instance the amount of antidote, the seasonal period of treatment and the type of composition.

Other factors influencing the practical aspects of the treatment are the type of cultivation to be protected, the non selective herbicide that is being used, the climatical and environmental conditions.

When the antidote is applied in a preventive treatment of the seeds, it may be used either as such or, preferably, in the form of a suitable compositions.

The compositions for the treatment of the seeds may be in the form of powders, wettable powders or as emulsifiable concentrates, and in general consist of the active compound in quantities comprised between 0.5% and 95% by weight, and of the usual inert carriers which, depending on the type of composition, may be solid such as: talc, silica, diatomite, bentonite, calcium carbonate and mixtures thereof, or liquids such as: water, alkyl-aromatic hydrocarbons, acetone, cyclohexanone and mixtures thereof.

In said compositions there may be present also suitable additives such as: surfactants, wetting agents, dispersants and mixtures thereof.

A specific example of a composition in a powdery form, for the treatment of the seeds (seed-dressing), is the following:

| | |
|---|---|
| compounds of formula I | 25–75% b.w. |
| mixture of a wetting agent with a | 1–5% b.w. |

-continued

| | |
|---|---|
| dispersant and an adhesivating agent | |
| solid inert carrier | 20-74% b.w. |

Examples of useful wetting agents are: polyoxyethylated nonyl-phenol, sodium alkylnaphthalenesulphonate, sodium alkylsulphosuccinate; examples of dispersing agents are: sodium, calcim or aluminum, lignosulphonate, sodium alkylnaphthalenesulphonate condensed with formaldehyde, maleic anhydride-diisobutylene co-polymers; examples of adhesivating agents are: glycols, glycerine, polyglycols, gum arabic, starch, sodium polymethacrylate of various molecular weight.

All the above listed additives are well known in the field of formulations and are commercially available also in the form of preconstituted mixtures.

The above cited compositions are prepared by mixing together the ingredients and by then homogenizing them by grinding up to the desired granulometry.

Said compositions may serve as such for the treatment of the seeds in the dry state or diluted in some water for a wet treatment.

As previously indicated, the amount of antidote to be distributed on the seeds, varies depending on different factors; in general, however, it is sufficient to use quantities of the product comprised between 0.1 and 100 g/kg of seeds.

The treatment carried out directly in the plant or on the medium on which it grows, obviously require the use of the antidote in the form of a suitable composition according to the normal procedures of this type of applications.

In applications in which the antidote is distributed on the plants or on the soil together wit the nonselective herbicide in one single formulation, the type of formulation and the content of it vary depending on the above indicated factors both with regard to the type of herbicide used as well as to its characteristics.

The amount of antidote to be used, in general is comprised between 0.1 and 10 kg/ha, while the ratio between antidote and herbicide in the composition may range from 1:5 to 5:1 by weight.

However, with reference to specific combinations between the cultivation to be protected, the type of nonselective herbicide and the relative efficacy of the compound of formula I taken into consideration, the quantity of antidote to be used for the treatment of the soil or on the cultivation may even be only just 10 g/ha while the antidote/herbicide ratio in the composition may be as low as a ratio near 1:1000 by weight.

For instance, compound N. 1 (see example 1) used in the treatment of the soil as antidote in the protection of maize cultivations from the toxic action of herbicide Eptam, proves effective even at the dose of 12 g/ha when used in admixture with the herbicide in the ratio of 1.5:1000.

The compounds of formula I, in general, are endowed with a wide action spectrum being effective as antidotes on a variety of useful crops such as, besides maize, wheat sorghum and beets.

During the tests we carried out, compounds of formula I showed also a certain biostimulating action on the treated plants. In order to better illustrate the invention in the following are given some examples.

In the data concerning 1H—NMR spectra reported in the examples, the following abbreviations were used: s=singlet, d=doublet, t=triplet, q=quartet, m=multiplet or complex unresolved signal, J=coupling constant.

EXAMPLE 1

Preparation of the methyl ester of (N-dichloroacetyl-2-methyl-1,3-thiazolidin-2-yl)-acetic acid (compound n. 1)

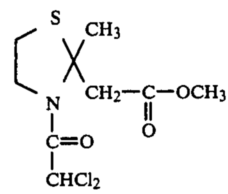

(A) Preparation of the methyl ester of (2-methyl-1,3-thiazolidine-2-il)-acetic acid To a suspension of cysteamine hydrochloride ($HS—CH_2—CH_2—NH_2.HCl$) (5,6 g, 0.05 moles) in anhydrous ethanol (100 ml) there was added a solution of methylacetacetate ($CH_3—CO—CH_2—COOCH_3$) (6 g; 0.051 mols) in anhydrous ethanol (10 ml). After 6 hours this solution was additioned with a solution of trethylamine (5 g, 0.05 mols) in anhydrous ethanol (20 ml).

This reaction mixture was then allowed to rest overnight. Thereafter, the solvent was removed by evaporation at reduced pressure and the residue was collected with ethyl ether (100 ml). The separated triethylammonium chlorohydrate was removed by filtration. Thereupon, the solvent was removed by evaporation at reduced pressure, thereby obtaining 7.2 grams of the desired product (IR and $^1H$—NMR were consistent with the assigned structure).

(B) Acylation of the product obtained according to point A

To a solution of methyl ester of (2-methyl-1,3-thiazolidine-2-yl)-acetic acid (3.2 g, 0.018 moles) and triethylamine (2 g, 0.02 moles) in methylene chloride ($CH_2Cl_2$) (30 ml) a solution of dichloroacetylchloride ($CHCl_2—COCl$) (3 g, 0.02 moles) in $CH_2Cl_2$ (20 ml) was added. The temperature was kept under 20° C.

Once the addition has been completed, the mixture was allowed to rest for 4 hours at room temperature. The mixture was then washed with water and dried on anhydrous sodium sulphate. The solvent was then removed by evaporation under reduced pessure.

The residue (5.1 g) was purified by chromatography on silica gel (eluent hexane/ethyl acetate) in the ratio 8:2).

Thereby were obtained 2.3 grams of Compound No. 1.

IR: meaningful bands at 1730 $cm^{-1}$ ($\nu COOCH_3$) and at 1670 $cm^{-1}$ ($\nu CON$).

$^1H$—NMR ($CDCl_3$, TMS)

$\nu$(ppm): 1.90 (s, 3H, C—$CH_3$), 3.08 (t, 2H, J=6 Hz, S—$CH_2$),

| | |
|---|---|
| 3.10 (d, 1H, J = 14 Hz) <br> 3.65 (d, 1H, J = 14 Hz) | $CH_2$—CO |

3.70 (s, 3H, $OCH_3$), 4.18 (t, 2H, J=6 Hz, N—$CH_2$), 6.17 (s, 1H, $CHCl_2$).

EXAMPLE 2

Preparation of ethyl ester of (2-methyl-N-dichloroacetyl-1,3-thiazolidin-2-yl)-acetic acid [compound No. 2]

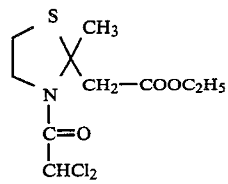

The product was prepared by a procedure analogous to the one described in example 1, starting from cysteamine hydrochloride and ethyl acetacetate, and by then acylating the obtained intermediate with dichloroacetyl chloride.

IR: meaningful bands at 1730 $cm^{-1}$ ($\nu COOC_2H_5$) and at 1675 $cm^{-1}$ ($\nu CON$).

$^1H$—NMR ($CDCl_3$, TMS)

$\nu$(ppm): 1.28 (t, 3H, J=8 Hz, $CH_2$—$CH_3$) 1.90 (s, 3H, C—$CH_3$), 3.08 (t, 2H, J=6 Hz, S—$CH_2$),

| | |
|---|---|
| 3.10 (d, 1H, J = 14 Hz)<br>3.65 (d, 1H, J = 14 Hz) | $CH_2CO$ |

4.15 (q, 2H, J=8 Hz, $CH_2$—$CH_3$), 4.18 (t, 2H, J=6 Hz, N—$CH_2$), 6.17 (s, 1H, $CHCl_2$).

EXAMPLE 3

Preparation of methyl ester of N-dichloroacetyl-2-phenyl-1,3-thiazolidine-2-carboxylic acid compound No. 3

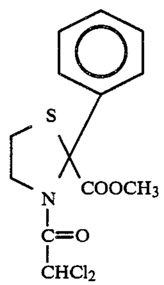

(A) Preparation of methyl ester of 2-phenyl-1,3-thiazolidine-2-carboxylic acid

A solution containing 3,3 g (0,02 moles) of methyl phenyl-glyoxylate in 20 ml of ethanol at 95% was added to a suspension containing 2.3 g (0,02 moles) of cysteamine chloridrate in 20 ml of ethanol at 95%.

The mixture was stirred at room temperature for 30 minutes, then 1,6 ml of pyridine were added. The resulting mixture was heated for 6 hours at 45° C.

After cooling the solvent was removed by evaporation at reduced pressure and the crude product was diluted with 10 ml of water and extracted by means of ethylether (3×20 ml).

The organic phases were collected and extracted with hydrochloric acid at 10% (2×10 ml).

The acid extract was neutralized with $NaHCO_3$.

Than it was extracted with ethyl ether (3×20 ml) and after evaporation of the solvent from the extract.

2,3 g of the desired product (white solid, m.p.=87°-88° C.) were obtained.

The spectroscopic data were consistent with the assigned structure.

(B) The intermediate obtained as in paragraph (A) was acylated with dichloroacetylchloride according to the procedure of Example 1, paragraph B to yield the desired product in the form of a solid m.p. 121°-2° C.

IR meaningful bands at 1735 $cm^{-1}$ ($\nu COOCH_3$) and 1670 $cm^{-1}$ ($\nu CO$—N). $^1H$—NMR ($CDCl_3$, TMS), $\nu$(ppm): 2.95-3.60 (m, 2H, S—$CH_2$), 3.82 (s, 3H, $OCH_3$), 3.9-4.9 (m, 2H, N—$CH_2$), 6.15 (s, 1H, $CHCl_2$), 7.2-7.7 (m, 5H, aromatic protons).

EXAMPLE 4

Preparation of benzyl N-dichloroacetyl-1,3-thiazolidine-2-carboxylate

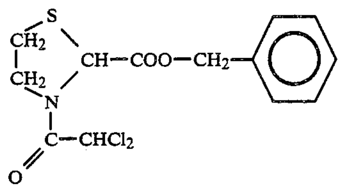

There was prepared a mixture consisting of:

5 g of N—dichloroacetyl—1,3—thiazolidine—2—carboxylic acid;

1,4 g of $K_2CO_3$;

3,4 g of benzyl bromide;

20 ml of 2-butanone.

The mixture was reflux heated while stirring for 3 hours.

After cooling, it was filtered and the solvent was removed by evaporation at reduced pressure.

7 g of crude product were obtained, which was purified by flash-chromatography, by using as eluent a mixture of hexane and ethyl acetate in a 2:1 volumetric ratio.

3,5 g of the desired product were obtained, which appeared as an oil; the spectroscopic data were consistent with the assigned structure.

EXAMPLE 5

Preparation of phenyl N-dichloroacetyl-1,3-thiazolidine-2-carboxylate (Compound N. 5)

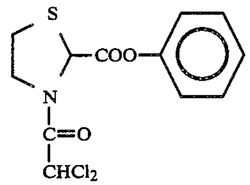

The compound was prepared by esterification of N-dichloroacetyl-1,3-thiazolidine-2-carboxyl acid with phenol in the presence of dicyclohexyl-carbodiimide and was obtained as a solid m.p. 96°-97° C.

IR meaningful bands at 1755 $cm^{-1}$ (νCOO) and 1670 $cm^{-1}$ (νCO—N)

EXAMPLE 6

In the following are reported other compounds of formula I prepared according to the procedures described in the preceding examples.

Compound No. 6

Benzyl N-benzoyl-1,3-thiazolidine-2-carboxylate

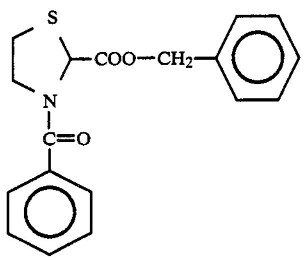

liquid at room temperature; IR meaningful bands at 1735 $cm^{-1}$ (νCOO) and 1640 $cm^{-1}$ (νCO—N).

Compound No. 7

4-chloro-benzyl N-dichloroacetyl-1,3-thiazolidine-2-carboxylate

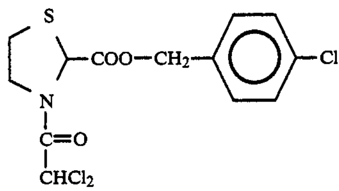

liquid at room temperature; IR meaningful bands at 1735 $cm^{-1}$ (νCOO), 1670 $cm^{-1}$ (νCO—N) and 800 $cm^{-1}$ (νCH aromatic).

Compound No. 8

Propargyl N-dichloroacetyl-1,3-thiazolidine-2-carboxylate

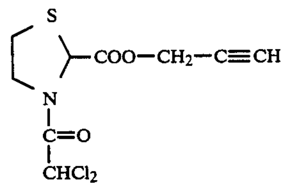

liquid at room temperature; IR meaningful bands at 3260 $cm^{-1}$ (ν≡C—H), 2120 $cm^{-1}$ (νC≡C), 1745 $cm^{-1}$ (νCOO) and 1670 $cm^{-1}$ (νCO—N).

Compound No. 9

Ethyl N-dichloroacetyl-2-methyl-1,3-thiazolidine-2-carboxylate

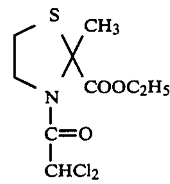

solid with m.p.=71,72° C.; IR meaningful bands at 1730 $cm^{-1}$ (νCOO) and 1670 $cm^{-1}$ (νCO—N).

$^1$H—NMR ($CDCl_3$, TMS)

δ(ppm): 1.25 (t, 3H, $CH_2$—$\underline{CH_3}$), 1.9 (s, 3H, $CH_3$), 2.8–3.6 (m, 2H, S—$CH_2$), 4.2 (q, 2H, $\underline{CH_2}$—$CH_3$), 3.7–4.7 (m, 2H, N—$CH_2$), 6.2 (s, 1H, $CHCl_2$).

Compound No. 10

Benzyl N-dichloroacetyl-2-methyl-1,3-thiazolidine-2-carboxylate

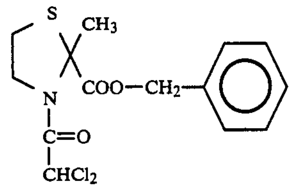

liquid at room temperature, IR: meaningful bands at 1730 $cm^{-1}$ (νCO—N) and 1665 $cm^{-1}$ (νCO—N)

$^1$H—NMR ($CDCl_3$, TMS)

δ(ppm): 1.9 (s, 3H, $CH_3$), 2.7–3.5 (m, 2H, S—$CH_2$), 3.6–4.7 (m, 2H, N—$CH_2$), 5.15 (s, 2H, O—$CH_2$), 6.12 (s, 1H, $CHCl_2$), 7.35 (s, 5H, aromatic protons).

EXAMPLE 7

Antidotic activity on maize plants by preventive treatment of the seeds.

General modalities: 60 maize seeds treated with 60 mg of the antidote to be tested, dissolved in 3 ml of an aqueus solution of dimethylsulfoxide (DMSO)) at 3% by weight, or in 3 ml of water optionally containing a wetting agent at 0,1%. On the basis of 60.000 seeds/ha the employed dose was corresponding to 60 g of antidote per hectare or was corresponding to 2,8 g of antidote per kg of seeds.

The treatment was carried out by mixing the seeds for 10 minutes in the solution and then by allowing them to dry for 24 hours, stirring them at intervals during the first hours.

The treated seeds were then sowed into a ground previously treated with the herbicide under examination, at the predetermined dose.

For purpose of a control, maize seeds, which had been left in a water bath not containing any antidote, under the same conditions, were sowed as well.

After a 10 day growth under continuous light and at a temperature of 25° C., the antidotic activity was evaluated by comparing the growth of the plants treated with the herbicide and with the herbicide plus the antidote, with the growth of the plants treated neither with the herbicide nor with the antidote.

The results recorded on the following Table 1 refer to the toxic action of the herbicide Eptam at the dose of 4 kg/ha in the presence of the antidote, on maize plants and are expressed according to a scale of values from 4

(complete stop of growth or death of the plant) to 0 (plant growth like the one of plants not treated with herbicide and antidote).

As a consequence, an evaluation equal to the one of the herbicide alone is indicative of the absence of an antidotic effect, while lower values are indicative of an antidotic effect increasing towards the lower values. Preliminary laboratory tests proved that the antidotes of formula I are not toxic for the maize and that the herbicide activity of Eptam towards the common infesting plants of the maize (*Solanum nigrum*, Amarantus spp, Echinocloa spp, Digitaria spp, Setaria spp, *Sorghum halepense, Panichum dichtomiflorum, Cyperus rotundus* and *Cyperus esculantus*) is not affected by the presence of the antidote in this kind of test.

TABLE I

Antidotic activity on maize by preventive treatment of the seed.

Herbicide: Eptam at a dose of 4 kg/ha.
Antidote: compound of formula I at a dose of 2,8 g/kg of seeds

| Compound No. (see preceding examples) | Toxic action of the herbicide (scale from 0 to 4) |
|---|---|
| — | 4 |
| 3 | 0 |
| 4 | 0 |
| 5 | 0 |
| 6 | 1 |
| 7 | 0 |
| 8 | 0 |
| 10 | 0 |

EXAMPLE 8

Antidotic activity on sorghum and on wheat, by treatment of the seeds.

There was prepared a composition for the treatment of the seeds consisting of:

| | | |
|---|---|---|
| Compound of formula I | 25% | b.w. |
| Polyoxyethylated nonylphenol | 0.5% | b.w. |
| Sodium lignosulphonate | 0.5% | b.w. |
| Glycerine | 0.1% | b.w. |
| Diatomite (fossil flour) | 73.9% | b.w. |

The compounds were mixed together and homogenized by grinding, until obtaining a thin powder.

The sorghum and wheat seeds were treated separately with the above described composition, in a dose of 10 g of active ingredient (Compound of formula I) per 1 kg of seeds.

The successive day the seeds thus treated were sown in pots containing sandy soil.

The pots were then treated by sprinkling them with a solution of herbicide Alachlor in dimethylsulphoxide, at a concentration corresponding to a practical dose of 0.75 and 1.5 kg/ha of herbicide.

For comparative purposes there were used a series of pots containing seeds that had not been treated neither with the herbicide nor with antidote and a series of pots containing seeds treated with the herbicide but not with the antidote.

All the pots were then kept in a conditioned environment, different for each sown plant, and more particularly, at 15°-24° C. and 70% relative humidity, with a photo period of 12 hours for wheat, and at 17°-31° C., 43-88% relative humidity, photoperiod of 15 hours for sorghum.

The pots were regularly watered in order to ensure a normal development of the plants.

After 3 weeks from the seeding it was proceeded with the determination of the antidotic activity by comparing the growth of the plants treated both with the antidote (on the seeds) as well as with the herbicide, with the growth of the plants that had not been treated or that had been treated only with the herbicide.

The results are expressed using the same scale of values (from 0 to 4) described in example 7.

Compounds No. 1 and 9 (see examples 1 and 6 respectively) showed, both on sorghum as well as on the wheat, a full antidotic activity (evaluation=0) against the damages caused by Alachlor at both the dose of 0.75 and 1.5 kg/ha.

At the same doses the herbicide Alachlor caused a complete stop of growth (rated 4) in the control plant in the absence of antidote.

EXAMPLE 9

Determination of the antidotic activity by treatment of the soil.

The test was carried out on maize of the Decalbe XL 72 A variety suitably sown in pots containing sandy soil. The sown pots were subdivided into three groups. One group was treated by sprinkling the soil with a commercial formulation of herbicide Eptam (in doses corresponding to 8 kg/ha of active ingredent) to which the compound of formula I to be tested was added at the selected concentration; the second group was treated with only the herbicide, while the third group was not treated, neither with the herbicide nor with the antidote and was used as control.

The pots were kept in a conditioned room (conditions corresponding to the springtime growth) at 15°-24° C., at a 70% relative humidity, photo period of 12 hours, and they were regularly watered to ensure a good germination.

After 10 days from the treatment, the antidotic activity was evaluated by comparing the growth of the plants and their vegetative state with respect to the plants treated only with the herbicide and to those left untreated.

The results have been expressed on the basis of the vegetative state of the plant by means of a scale of values ranging from 4 (complete stop of growth or death of the plant) to 0 (healthy plant, growth equal to that of the control plant grown in the absence of herbicide and antidote). Thus, a numerical evaluation equal to that of the plant treated with the herbicide only, indicates a lack of antidotic activity, while an evaluation equal to zero indicates a full protection of the plant from the toxic action of the herbicide. The intermediate values indicate an only partial antidotic effect that increases towards the lower values.

Preliminary laboratory tests have shown that the antidotes of formula I are not toxic for maize and that the herbicide activity of Eptam towards the common infesting weeds of maize (*Solanum Nigrum*, Amarantus spp., Echinochloa spp., Digitaria spp., Setaria spp., *Sorghum halepense, Panichum dichotomiflorum, Cyperus rotundus* and *Cyperus esculantus*) is not influenced by the presence of the antidote in this type of test.

Compounds No. 1, 2 and 9 (see examples 1, 2 and 6 respectively) showed a full antidotic activity (growth of the plant equal to that of the control plant, evaluation=0) at a dose of 80 g/ha (1% by weight with respect to the herbicide) while herbicide Eptam, at the considered dose, caused a total stop of the growth of the plants (evaluation=4).

What we claim is:

1. A compound of formula:

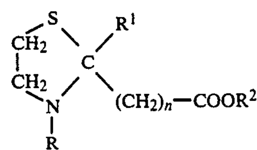

wherein:

R represents the group $$-\underset{\underset{O}{\|}}{C}-R^3$$

in which $R^3$ is a $C_1$–$C_3$ haloalkyl containing from 1 to 3 halogen atoms or phenyl;

$R^1$ represents a hydrogen atom, methyl or phenyl;

$R^2$ represents a $C_1$–$C_8$ alkyl, $C_5$–$C_6$ cycloalkyl, cyclohexyl methyl, phenyl, benzyl, allyl or propargyl optionally substituted with halogen atoms;

n is zero or one;

provided that, when contemporaneously R is a haloacetyl group, $R^1$ is hydrogen, and n is zero, $R^2$ is different from a $C_1$–$C_4$ alkyl.

2. A compound according to claim 1, in which n is zero.

3. A compound according to claim 2 in which R is dichloroacetyl.

4. A compound according to claim 2 in which R is benzoyl.

5. A compound according to claim 4 and which is benzyl N-benzoyl-1,3-thiazolidine-2-carboxylate.

6. A compound according to claim 1 in which n is one.

7. A compound according to claim 6 in which R is dichloroacetyl.

8. A compound according to claim 7 and which is the methyl ester of (N-dichloroacetyl-2-methyl-1,3-thiazolidin-2-yl)-acetic acid.

* * * * *